United States Patent
Tan

(10) Patent No.: US 9,949,938 B2
(45) Date of Patent: Apr. 24, 2018

(54) COQ10 (UBIQUINONE, UBIQUINOL), VITAMIN A (RETINOID ACID, RETINOL), VITAMIN E (TOCOTRIENOL, TOCOPHEROL) AND METHODS OF USE

(71) Applicant: AMERICAN RIVER NUTRITION, Hadley, MA (US)

(72) Inventor: Barrie Tan, Amherst, MA (US)

(73) Assignee: AMERICAN RIVER NUTRITION, Hadley, MA (US)

( * ) Notice: Subject to any disclaimer, the term of this patent is extended or adjusted under 35 U.S.C. 154(b) by 0 days.

(21) Appl. No.: 15/237,617

(22) Filed: Aug. 15, 2016

(65) Prior Publication Data

US 2017/0027882 A1    Feb. 2, 2017

Related U.S. Application Data

(63) Continuation of application No. 14/323,887, filed on Jul. 3, 2014, now abandoned.

(60) Provisional application No. 61/842,732, filed on Jul. 3, 2013.

(51) Int. Cl.
| | | |
|---|---|---|
| *A61K 31/09* | (2006.01) | |
| *A61K 31/122* | (2006.01) | |
| *A61K 31/05* | (2006.01) | |
| *A61K 31/07* | (2006.01) | |
| *A61K 31/352* | (2006.01) | |
| *A61K 31/353* | (2006.01) | |
| *A61K 31/355* | (2006.01) | |
| *A61K 31/593* | (2006.01) | |
| *A61K 47/24* | (2006.01) | |
| *A61K 9/06* | (2006.01) | |

(52) U.S. Cl.
CPC ............... *A61K 31/09* (2013.01); *A61K 9/06* (2013.01); *A61K 31/05* (2013.01); *A61K 31/07* (2013.01); *A61K 31/122* (2013.01); *A61K 31/352* (2013.01); *A61K 31/353* (2013.01); *A61K 31/355* (2013.01); *A61K 31/593* (2013.01); *A61K 47/24* (2013.01)

(58) Field of Classification Search
CPC .................................................... A61K 31/355
See application file for complete search history.

(56) References Cited

U.S. PATENT DOCUMENTS 7,989,006 B2 * 8/2011 Tan ..................... A61K 31/22
                                                        424/725

* cited by examiner

*Primary Examiner* — Bin Shen
(74) *Attorney, Agent, or Firm* — Kirk Hahn

(57) ABSTRACT

CoQ10 and vitamin E are both lipid-soluble nutrients with redox potential. Tocopherol and/or tocotrienol protect CoQ10 from oxidative damage and reduce ubiquinone in situ. Specifically, vitamin E protects the oxidation of ubiquinol to ubiquinone ex vivo and reduces ubiquinone to ubiquinol in situ. Vitamin Es with higher ratio of tocotrienol-to-tocopherol cause a higher ratio of ubiquinol-to-ubiquinone. Additionally tocopherol and/or tocotrienol protect vitamin A oxidation from retinol to retinoic acid.

7 Claims, 4 Drawing Sheets

COQ10 (UBIQUINONE, UBIQUINOL), VITAMIN A (RETINOID ACID, RETINOL), VITAMIN E (TOCOTRIENOL, TOCOPHEROL) AND METHODS OF USE

CROSS-REFERENCE TO RELATED APPLICATIONS

This application is a Continuation of U.S. Non-Provisional application Ser. No. 14/323,887 filed on Jul. 3, 2014, which claims priority upon U.S. Provisional Patent application Ser. No. 61/842,732 filed on Jul. 3, 2013, the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

Co-enzyme Q10 (CoQ10) is a co-enzyme; a substance in the body that assists the function of an enzyme or enzyme system. CoQ10 was discovered in 1957, and its molecular structure was determined in 1958 to be 2,3-dimethoxy-5-methyl-6-decaprenil-1,4-benzoquinone. Its biological presence was ubiquitously found in the body and because of its ubiquitous nature, CoQ10 came to be known as ubiquinone. CoQ10 exists in at least 3 distinct chemical entities; ubiquinol (reduced state product), semiquinone radical (1-electron oxidation product), and ubiquinone (2-electron oxidation product). Ubiquinone and ubiquinol are located on the inner membrane of the mitochondria, an intracellular organelle.

CoQ10 is a classic lipophilic antioxidant, like vitamin E. In an analogous fashion, vitamin E exists in the same 3 chemical identities as CoQ10; tocotrienol or tocopherol (reduced state product), chromanoxyl (i.e., tocotrienoxyl or tocopheroxyl) radical (1-electron oxidation product), and chromanoxyl quinone (2-electron oxidation product). This is exemplified in Table 1. Interestingly, CoQ10 and tocotrienol contain 10 and 3 isoprene units in their lipophilic tail, respectively.

TABLE 1

| Lipophilic Compound | Reduced Product | Intermediate (1-electron oxidation) product | Oxidized (2-electron oxidation) product |
|---|---|---|---|
| Co-enzyme Q10* | Ubiquinol | Semiquinone radical | Ubiquinone |
| Vitamin E (Chromanol) | | | |
| Tocotrienol (T3)* | Tocotrienol | Tocotrienoxyl radical | Tocotrienoxyl quinone |
| Tocopherol (T) | Tocopherol | Tocopheroxyl radical | Tocopheroxyl quinone |

*CoQ10 and T3; their numeric designations indicate 10 and 3 repeating isoprene units, respectively.

Redox enzymes in the body are quite capable of interconverting ubiquinone to ubiquinol, and vice versa. For example, ubiquinone is the substrate for NADH dehydrogenase, and ubiquinol is the substrate for cytochrome c reductase. Similarly, there may be redox enzymes in the body that interconvert chromanoxyl quinone (vitamin E quinone) to chromanol (vitamin E), and vice versa. This is the biochemical and/or biological situation in vivo.

Chemically, ubiquinol is unstable (prone to oxidation), but chromanol is relatively more stable. Both of these lipid-soluble antioxidants are found embedded in membranes and in lipoprotein particles. Ascorbic acid and alpha-lipoic acid are known to protect vitamin E on the hydrophilic domain of the cytosolic membrane surfaces, converting any oxidized products back to the reduced alcohol products. However, in the lipid domain, ubiquinone-ubiquinol and tocopherol-tocotrienol protect lipid peroxidation, and they have only each other to interconvert within the lipid domain.

CoQ10 is critically needed for energy transduction and oxidative phosphorylation, so its role as an antioxidant is secondary. In the lipid domain, tocotrienol and tocopherol are the foremost and critical antioxidants. Both CoQ10 and vitamin E are carried in the phospholipids of lipoprotein particles throughout the arterial blood vessels, and there are 30,000 miles of these vessels throughout the body. Therefore, both vitamin E and CoQ10 are also delivered ubiquitously to many organs (e.g., heart, kidney, liver, pancreas, muscle, skin, plasma and adipose tissues).

CoQ10 in normal healthy adults is in the reduced ubiquinol form. This is the form our body requires for its metabolic utilization. Supplemental CoQ10 pills sold in stores are in the oxidized ubiquinone form. Normally, the body is capable of converting the oxidized ubiquinone form to the reduced ubiquinol form. Therefore, taking supplements of ubiquinone will suffice, since the healthy body reduces ubiquinone to ubiquinol. However, with age, oxidative stress and chronic inflammation, the body's ability to convert ubiquinone to ubiquinol is compromised (FIG. 1A). Supplemental ubiquinol are particularly useful to compensate for individuals with a reduced ability to convert ubiquinone to ubiquinol in the body.

Physiologically, the body reduces ubiquinone (a ketone) to ubiquinol (an alcohol), which is the active form of CoQ10 used during mitochondrial respiration. The addition of a vitamin E (e.g., tocotrienol) protects the labile oxidation of ubiquinol to ubiquinone, and furthermore, reduces ubiquinone to ubiquinol in situ (i.e., in softgels or other combinatory formulations) (FIG. 1B).

Physiologically, the body absorbs preformed vitamin A (retinol) or plant-derived intact beta-carotene and converts it to the useful form—retinol. Chemically, two molecules of retinol are in one molecule of beta-carotene. An enzyme in our body, beta-carotene deoxygenase, hydrolyses beta-carotene into two molecules of retinol. Vitamin A has many utilities, such as, cellular differentiation, immunity, skin health, and the most known use, sight. Retinol is the reduced state of vitamin A whereas retinoic acid is the oxidized state of vitamin A. Unlike the nontoxic CoQ10 couple, retinoic acid is toxic, and hence there is a cautionary limit to retinol consumption. The physiological role of retinoic acid in the body remains controversial or, at best, is uncertain. There have been some examples of the deleterious role of vitamin A (retinoic acid) in the body.

In preparation for lactation, expectant mothers store retinoids in the liver and breast. Breastfeeding allows the transfer of stored retinoids to infants for proper growth, immunity against pathogens, and sight in the world outside the womb. Thus, there is a natural process in place for reducing toxic accumulation of retinoids in mothers, averting hypervitaminosis A. It has been theorized that maternal hypervitaminosis A—primarily caused by a backup of retinoic acid—causes postpartum depression, a condition that affects 1 in 8 mothers.

Malaria is the most significant public health problem in the world with nearly 3.5 billion (1 in 2) people at risk. The malaria parasite absorbs vitamin A and converts it to retinoic acid for its use to invade the red blood cells. Listlessness from anemia in patients is the hallmark symptom of the disease. It has been theorized that hypervitaminosis A—from a backup of retinoic acid produced by the parasite—causes or exacerbates the symptoms in the person.

It is therefore understood that the oxidized form of vitamin A, retinoic acid, is detrimental. Furthermore, vitamin A in its reduced form (retinol) should be maintained for its essential functions in the body (FIG. 1C).

BRIEF SUMMARY OF INVENTION

In one embodiment, vitamin E (tocotrienol and tocopherol) is used to reduce ubiquinone to ubiquinol in situ, and furthermore, to protect the oxidation of ubiquinol to ubiquinone ex vivo.

In another embodiment tocotrienol is used in combination with ubiquinol, in vivo, for use in systemic circulation, where the ubiquinol is stabilized and tocotrienol preserves ubiquinol from oxidative losses.

In another embodiment tocotrienol is used in combination with ubiquinol, in the gastrointestinally ex systemic circulation, where the ubiquinol is preserved and tocotrienol protects acid-induced degradation to other oxidized products of CoQ10.

In another embodiment tocotrienol is used in combination with ubiquinone, in a mixture (e.g., in a softgel) where ubiquinone is converted to ubiquinol, and tocotrienol reduces the ubiquinone in situ.

In another embodiment vitamin E (tocotrienol and tocopherol) is used to protect the oxidation of retinol to retinoic acid in situ, and furthermore, reduces retinoic acid to retinol in vivo.

In one embodiment, ubiquinone is present at 20-150 mg/unit (softgel) in an encapsulated supplement mixture. In another embodiment ubiquinone is present at 10-500 mg/unit (softgel) in an encapsulated supplement mixture.

In one embodiment, tocotrienol is present at 1-1,000 mg/unit (softgel) in an encapsulated supplement mixture. In another embodiment tocotrienol is present at 10-300 mg/unit (softgel) in an encapsulated supplement mixture. In another embodiment tocotrienol is present at 30-180 mg/unit (softgel) in an encapsulated supplement mixture.

In one embodiment, some of the ubiquinone will convert to ubiquinol in the formulation. In another embodiment more than 25% of the ubiquinone is converted to ubiquinol. In another embodiment as much as 85% to 95% of the ubiquinone is converted to ubiquinol. In another embodiment, on average about 50% of the ubiquinone is converted to ubiquinol.

In one embodiment, tocotrienol is combined with ubiquinone, in a mixture (e.g., in a softgel) where ubiquinone is converted to ubiquinol, and thereby tocotrienol reduces the ubiquinone in situ. In another embodiment tocopherol is combined with ubiquinone, in a mixture (e.g., in a softgel) where ubiquinone is converted to ubiquinol, and thereby tocotrienol reduces the ubiquinone in situ.

In one embodiment, tocotrienol and CoQ10 are combined with omega-3 fatty acids at 100-1,500 mg/softgel. In another embodiment, tocotrienol and CoQ10 are combined with omega-3 fatty acids at 100-1,000 mg/softgel. In another embodiment, tocotrienol and CoQ10 are combined with omega-3 fatty acids at 250-500mg/softgel.

In one embodiment, vitamin E is combined with vitamin A to protect the retinol from oxidation to retinoic acid in an encapsulated supplement mixture. In another embodiments, vitamin E is present at 50-300 mg/unit (softgel) in the encapsulated supplement mixture. In another embodiments, vitamin E is present at 100-200 mg/unit (softgel) in the encapsulated supplement mixture. In another embodiments, vitamin A is present at 500-5,000 IU/unit (softgel) in the encapsulated supplement mixture. In another embodiments, vitamin A is present at 1,000-5,000 IU/unit (softgel) in the encapsulated supplement mixture.

DETAILED DESCRIPTION OF THE INVENTION

Figure 1A:
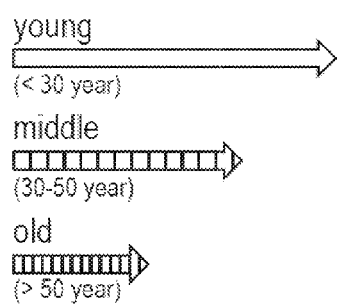
FIG. 1A illustrates the body's normal physiological enzymatic conversion of ubiquinone to ubiquinol in young, middle-aged, and old individuals. The in vivo conversion of ubiquinone to ubiquinol in the body decreases with age. Shorter arrows indicate less conversion to the desirable body-required ubiquinol.
Figure 1B:
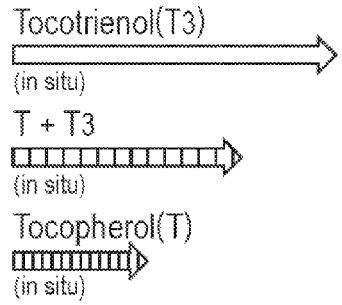
FIG. 1B illustrates that outside the body; vitamin E converts and reduces ubiquinone to ubiquinol. This conversion is better with tocotrienols (e.g., annatto extracts) than tocopherol-tocotrienol mixtures (e.g., palm extracts), and in turn better than tocopherols (e.g., soy extracts).
Figure 1C:
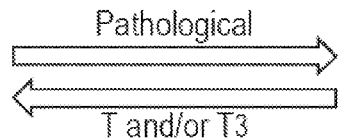
FIG. 1C illustrates the abnormal pathological conversion of retinol to retinoic acid, which is potentially toxic. The addition of vitamin E (tocopherols or tocotrienols) resists oxidation and keeps the vitamin A in its retinol form.

Vitamin E (tocotrienol and tocopherol) protects phytonutrients from oxidation and reduces phytonutrients into their active forms. This can be done endogenously (in vivo), as well as, exogenously (ex vivo). FIGS. 1A-C illustrate this protection and reduction.

Oxidative stress is a phrase used to bring focus to the imbalance caused by oxidants from physiologic conditions (e.g., strenuous exercise, trauma), exposure to environmental stress (e.g., UV light, ozone, smoke, pollutants), infectious organisms, and the aging process. The free radical theory of aging underscores many of these oxidative stresses that manifest in degenerative processes that accumulate over a lifetime. Therefore, disease implications of oxidative stress include pathogenic infections, as well as, degenerative and chronic disorders.

An example of oxidative stress is the oxidation of Low Density Lipoprotein (LDL) particles, which has been implicated for the origin of atherosclerosis. Treatment with ubiquinone led to an increase of LDL ubiquinol, which increased the resistance to LDL oxidation and in turn prevented the loss of vitamin E. It was concluded that while ubiquinol is capable of directly inhibiting lipid peroxidation, its main role was to amplify/regenerate vitamin E. CoQ10 is therefore a well-known lipid antioxidant. Surprisingly, it is unknown if the reverse can be expected, that is, vitamin E regenerates ubiquinone to ubiquinol. Tocotrienol has been shown to increase CoQ10 endogenously. This discovery shows that tocotrienol converts (or reduces) ubiquinone to ubiquinol in situ.

Although they are both lipid antioxidants, tocopherol is approximately 90 times more abundant than ubiquinol in the LDL particle. Strategically, tocopherol should be used as an oxidative protectant, and CoQ10 should be used as an energy transducer. Furthermore, tocotrienol is approximately 50 times more potent as an antioxidant than tocopherol. Strategically, tocotrienol should be more potent than tocopherol to preserve CoQ10 for energetics, and delta-tocotrienol and gamma-tocotrienol are the 2 most potent vitamin E antioxidant isomers. Therefore, delta-tocotrienol and gamma-tocotrienol can replace other vitamin E isomers to preserve CoQ10 for energetics.

Tocotrienol causes a higher degree of membrane disorganization, possibly because of the shorter farnesyl tail (as opposed to tocopherol's longer phytyl tail), which allows increased mobility. This increased mobility allows tocotrienol a greater accessibility to oxidized products of CoQ10 to convert them back to ubiquinol (Table 1). Preserving and protecting CoQ10, especially ubiquinone, is particularly critical because each LDL particle has many more times vitamin E than CoQ10, where the vitamin E:CoQ10 ratio is 88:1. Therefore, the role of vitamin E antioxidant is to prevent the loss of CoQ10 through oxidation and convert CoQ10 from ubiquinone to ubiquinol because of the antioxidant power of vitamin E tocopherol. Surprisingly, this concept is unknown. Furthermore, this advantage can be extended using the superior antioxidant power of vitamin E tocotrienol.

There exist situations where ubiquinol can be degraded by physical or chemical means ex vivo (i.e., not in systemic circulation). For example, under acidic conditions (pH<2) of gastric acids, ubiquinol undergoes acid-induced oxidation to ubiquinone. In as short as 30 minutes under gastric conditions, about 50% (from 25% to 75%) of ubiquinol is converted to ubiquinone. This half-hour is shorter than the typical two-hour residence before gastric discharge upon food consumption when a lipophilic substance/vitamin (like CoQ10) is concomitantly consumed. It is expected then that consumed ubiquinol will convert to oxidized ubiquinone (average 50%; range from 25% to 75%), during the two-hour stomach residence in the presence of gastric juices.

However, when tocotrienol is added in combination with ubiquinol, the tocotrienol resists the oxidative damage to ubiquinol. Tocotrienol can be used in combination with ubiquinol, in the gastrointestinally ex systemic circulation, where ubiquinol is preserved and tocotrienol protects acid-induced degradation to CoQ10 oxidized products.

Many more products are formulated with ubiquinone, the existing oxidized product of CoQ10. There are many advantages to a combination with tocotrienol, including but not limited to:

CoQ10 lowers systolic and diastolic blood pressure,
Tocotrienol reduces lipid peroxidation and spontaneous hypertension,
Tocotrienol lowers systolic blood pressure,
Tocotrienol increases arterial integrity,
Tocotrienol regulates natriuresis,
Tocotrienol increases CoQ10 levels, and
CoQ10 recycles tocotrienol.

The body is capable, via its redox enzymatic system, to reduce ubiquinone to ubiquinol, because, in the body, it is ubiquinol, not ubiquinone, that is utilized. The existence of synthesized or biosynthesized CoQ10 ubiquinol products in the marketplace underscores the importance of this reduced state coenzyme in the body. It is therefore highly desirable to convert ubiquinone to ubiquinol ex vivo prior to ingestion. Surprisingly, this challenge was not addressed and has not been exploited.

When ubiquinone (10-500 mg/unit (softgel)) is combined with tocotrienol (1-1,000 mg/unit (softgel)) in an encapsulated supplement mixture (e.g., in a softgel formulation), some of the ubiquinone will convert to ubiquinol in the formulation. More than 25% of the ubiquinone is converted to ubiquinol. As much as 85% to 95% of the ubiquinone is converted to ubiquinol. On average, 50% of the ubiquinone is converted to ubiquinol. Tocotrienol is combined with ubiquinone, in a mixture (e.g., in a softgel) where ubiquinone is converted to ubiquinol, and thereby tocotrienol reduces the ubiquinone in situ. This situation is also true when tocopherol is used, although the ubiquinone to ubiquinol reduction is less than when tocotrienol is used.

This discovery is significant because no synthesis is needed and no chemicals are needed for the manufacture of ubiquinol; just using the capability of tocotrienol and tocopherol as an inherent reductant (antioxidant) to reduce ubiquinone to ubiquinol, and to protect ubiquinol from oxidizing to ubiquinone.

This observed process also is important because:
ubiquinol is the form our body uses,
ubiquinol is the more potent antioxidant CoQ10,
ubiquinol is significantly more expensive and more unstable, and
unstable ubiquinol is manufactured "entombed" in the softgel since softgels exclude oxygen, air, and water.

In other words, vitamin E (tocopherols and tocotrienols) prevents oxidation of any ubiquinone or ubiquinol in the formula (nutritional supplement product), and vitamin E (tocopherols and tocotrienols) prevents or resists conversion of ubiquinone to ubiquinol.

Therefore, vitamin E (tocopherol and tocotrienol) protects phytonutrients from oxidation and reduces phytonutrients into its active forms. This can be done endogenously (in vivo) as well as exogenously (ex vivo). The latter is one of the discoveries disclosed in the application. Additionally, vitamin E (tocotrienol and tocopherol) protects the oxidation of retinol to retinoic acid in situ, and furthermore, reduces retinoic acid to retinol in vivo.

There are numerous published methods to stabilize CoQ10 (almost exclusively ubiquinone and to a much lesser extent ubiquinol). Most of these have to do with emulsification methods, largely to enable CoQ10 to be bioavailable (e.g. U.S. Pat. Nos. 6,740,338; 6,417,233; 6,056,971). However, none address protection (degradation of CoQ10), and when they did mention antioxidants, the antioxidants were esterified vitamin E (e.g., with lipoate, ascorbate, succinate, acetate, palmitate) that do not work to protect CoQ10. Furthermore, none addressed the novel concept of CoQ10 protection by conversion of ubiquinone to ubiquinol in situ, a reduction process within the softgels upon encapsulation.

This discovery obviates any need of the oxidation-prone emulsification step for ubiquinone or the prior use of the exceedingly unstable and expensive synthesis step for ubiquinol.

In one embodiment, vitamin E (tocotrienol and tocopherol) is used to reduce ubiquinone to ubiquinol in situ, and furthermore, to protect the oxidation of ubiquinol to ubiquinone ex vivo.

In another embodiment tocotrienol is used in combination with ubiquinol, in vivo, for use in systemic circulation, where the ubiquinol is stabilized and tocotrienol preserves ubiquinol from oxidative losses.

In another embodiment tocotrienol is used in combination with ubiquinol, in the gastrointestinally ex systemic circulation, where the ubiquinol is preserved and tocotrienol protects acid-induced degradation to other oxidized products of CoQ10.

In another embodiment tocotrienol is used in combination with ubiquinone, in a mixture (e.g., in a softgel) where ubiquinone is converted to ubiquinol, and tocotrienol reduces the ubiquinone in situ.

In another embodiment vitamin E (tocotrienol and tocopherol) is used to protect the oxidation of retinol to retinoidretinoic acid in situ, and furthermore, reduces retinoic acid to retinol in vivo.

In one embodiment, ubiquinone is present at 20-150 mg/unit (softgel) in an encapsulated supplement mixture. In another embodiment ubiquinone is present at 10-500 mg/unit (softgel) in an encapsulated supplement mixture.

In one embodiment, tocotrienol is present at 1-1,000 mg/unit (softgel) in an encapsulated supplement mixture. In another embodiment tocotrienol is present at 10-300 mg/unit (softgel) in an encapsulated supplement mixture. In another embodiment tocotrienol is present at 30-180 mg/unit (softgel) in an encapsulated supplement mixture.

In one embodiment, some of the ubiquinone will convert to ubiquinol in the formulation. In another embodiment more than 25% of the ubiquinone is converted to ubiquinol. In another embodiment as much as 85% to 95% of the ubiquinone is converted to ubiquinol. In another embodiment 50% on average of the ubiquinone is converted to ubiquinol.

In one embodiment, tocotrienol is combined with ubiquinone, in a mixture (e.g., in a softgel) where ubiquinone is converted to ubiquinol, and thereby tocotrienol reduces the ubiquinone in situ. In another embodiment tocopherol is combined with ubiquinone, in a mixture (e.g., in a softgel) where ubiquinone is converted to ubiquinol, and thereby tocotrienol reduces the ubiquinone in situ.

In one embodiment, tocotrienol and CoQ10 are combined with omega-3 fatty acids at 100-1,500 mg/softgel. In another embodiment, tocotrienol and CoQ10 are combined with omega-3 fatty acids at 100-1,000 mg/softgel. In another embodiment, tocotrienol and CoQ10 are combined with omega-3 fatty acids at 250-500 mg/softgel.

In one embodiment, vitamin E is combined with vitamin A to protect the retinol from oxidation to retinoidretinoic acid in an encapsulated supplement mixture. In another embodiments, vitamin E is present at 50-300 mg/unit (softgel) in the encapsulated supplement mixture. In another embodiments, vitamin E is present at 100-200 mg/unit (softgel) in the encapsulated supplement mixture. In another embodiments, vitamin A is present at 500-5,000 IU/unit (softgel) in the encapsulated supplement mixture. In another embodiments, vitamin A is present at 1,000-5,000 IU/unit (softgel) in the encapsulated supplement mixture.

Additional embodiments are described in the following paragraphs.

Paragraph 1. A composition comprising a chromanol and a CoQ10; whereby the chromanol converts some of the CoQ10 to ubiquinol and protects CoQ10 from degradation.

Paragraph 2. The composition of Paragraph 1, wherein the chromanol is vitamin E.

Paragraph 3. The composition of Paragraph 2, wherein the vitamin E is tocopherol.

Paragraph 4. The composition of Paragraph 2, wherein the vitamin E is tocotrienol.

Paragraph 5. The composition of Paragraph 1, wherein the CoQ10 is ubiquinone.

Paragraph 6. The composition of Paragraph 1, wherein more than 25% of the ubiquinone is converted to ubiquinol.

Paragraph 7. The composition of Paragraph 3, wherein the tocopherol is selected from the group of sources consisting of soy, corn, cottonseed, sunflower, natural (d-tocopherol), synthetic (dl-tocopherol), isolated isomers of tocopherol, and mixtures thereof.

Paragraph 8. The composition of Paragraph 4, wherein the tocotrienol is selected from the group of sources consisting of annatto, rice, and palm, natural (d-tocotrienol), synthetic (dl-tocotrienol), isolated isomers of tocotrienol, and mixtures thereof.

Paragraph 9. The composition of Paragraph 1, wherein the composition is selected from the group consisting of a softgel, tablet, two-piece gelatin shell, droplet, tincture oil, lotion, ointment, paste, powder, injectable, sublingual tablets, and sublingual drops.

Paragraph 10. The composition of Paragraph 9, wherein the composition is a softgel.

Paragraph 11. The composition of Paragraph 1, further comprising a fatty acid.

Paragraph 12. The composition of Paragraph 11, the fatty acid is selected from the group consisting of natural omega-3, synthesized omega-3, esterified omega-3, phospholipids, re-esterified, and structured lipids.

Paragraph 13. The composition of Paragraph 1, further comprising a component selected form the group consisting of vitamin A, vitamin D, vitamin K, isoprenes, geraniols, farnesols, geranylgeraniol, menaquinones, non-vitamin antioxidants, epigallocatechin gallate (EGCG), resveratrol, and quercetin.

Paragraph 14. A composition comprising a chromanol and a vitamin A retinol; whereby the chromanol reduces oxidation of vitamin A retinol to retinoic acid Paragraph 15. A method to protect ubiquinol in the stomach, comprising the steps of combining ubiquinol with a chromanol in an ingested formulation and ingesting the formulation.

Paragraph 16. A method comprising the step of combining a vitamin E into a mixture containing vitamin A, wherein the vitamin E protects the vitamin A oxidation from retinol to retinoic acid in situ.

Paragraph 17. A method comprising the step of combining a vitamin E into a mixture containing a vitamin A, wherein the vitamin E protects the vitamin A oxidation from retinol to retinoic acid ex vivo.

Paragraph 18. A method comprising the steps of combining a vitamin E into an ingestible mixture containing CoQ10 and emulsifiers to increase CoQ10's bioavailability, wherein the vitamin E protects the CoQ10 from loss of content and oxidation to the ubiquinone form due to the emulsification process.

Paragraph 19. A method comprising the steps of combining a vitamin E into a mixture containing CoQ10 and emulsifiers to increase CoQ10's bioavailability, wherein the vitamin E converts ubiquinone to ubiquinol.

EXAMPLES

Example 1

CoQ10 encapsulated supplements with various mixtures of vitamin E (tocopherol-free tocotrienols, tocopherol-tocotrienol mixtures, tocotrienol-free tocopherols, esterified vitamin E) were analyzed for ubiquinol and ubiquinone simultaneously by high performance liquid chromatography (HPLC) using a modified method of an existing collaborative study (Lunetta and Roman, 2008). Samples were prepped by expelling contents from softgels/capsules and transferring them quantitatively to a volumetric flask. Softgels were then rinsed exhaustively using ethanol, and rinses were transferred to the flasks. Sonication was used as needed to completely clean out the gels. Samples were standardized to volume with ethanol, then the flasks were stoppered and mixed thoroughly. Samples were diluted and immediately injected (20 uL injection volume) onto an HPLC manufactured by Thermo Separation Products with in-line degasser, P4000 pump, AS3000 Autosamples, and scanning detector. The column used was a Hypersil C18, 150 mm×4.6 mm, with 5 µm particle and 120 A pore size, which was used at ambient temperature. The mobile phase consisted of 80:15:5 acetonitrile:methanol:tetrahydrofuran with ammonium acetate (0.1%) and triethylamine (0.1%) added. The UV detection was 290 nm for ubiquinol and 275 nm for ubiquinone, and retention times were 28 minutes for ubiquinol and 35 minutes for ubiquinone. The method was designed to allow a view of both analytes in the same injection, either through a programmed wavelength shift or by simultaneously monitoring both 275 nm and 290 nm.

To date, most of the methods of analysis of CoQ10 is for ubiquinone, the oxidized version (Kaplan et al., 1996), as analysis of ubiquinol is difficult and remains elusive. There are at least two persistent difficulties. First, ubiquinol—the form that is central to physiological utility—is exceedingly unstable. Therefore, this compound is usually not analyzed. Second, analytical workup procedures (10-12 steps) are usually lengthy and with significant air exposure, where the steps taken would have introduced oxidation to make the analysis of ubiquinol reliable.

However, the method used in this study is a modification (Craft Technologies, Inc., 2014) of an existing collaborative study (Lunetta and Roman, 2008). Modifications were made to ensure the reliability of ubiquinol and ubiquinone analyses. These modifications include, but are not limited to:

1. Shortest sample preparation (2-3 steps)
2. "Dilute and inject"
3. No solvent evaporation required
4. Use of an in-line degasser
5. Dual wavelength monitoring (290 nm for ubiquinol and 275 nm for ubiquinone)
6. Simultaneous analysis of CoQ10 isomers, not two different analyses
7. Quickest possible time lapse from softgel-to-HPLC This modified method of an existing collaborative study allowed the unequivocal and reliable determination of both CoQ10 isomers, especially the unstable ubiquinol, necessary to substantiate the novelty of this discovery.

Figure 2:
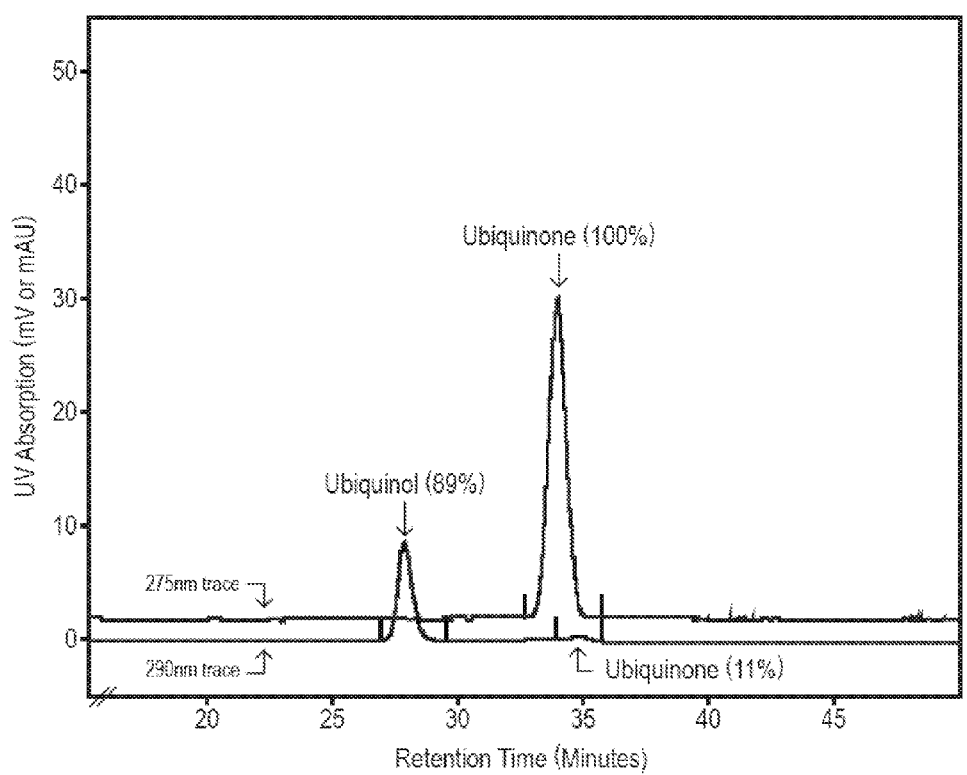
FIG. 2 illustrates HPLC analysis of a sample softgel containing 50mg CoQ10 and 50 mg tocotrienol. The analysis showed 89% of ubiquinol and 11% of ubiquinone when the UV was set at 290 nm (lower trace). The work-up sample was further deliberately oxidized, wherein all CoQ10 isomers converted to ubiquinone. HPLC analysis of this fully oxidized sample showed 100% ubiquinone when the UV was set at 275 nm (upper trace). This unequivocally proves that the ubiquinol and ubiquinone represent the true vitamin E protection of CoQ10 isomers and the conversion of ubiquinone to ubiquinol.
Figure 3:
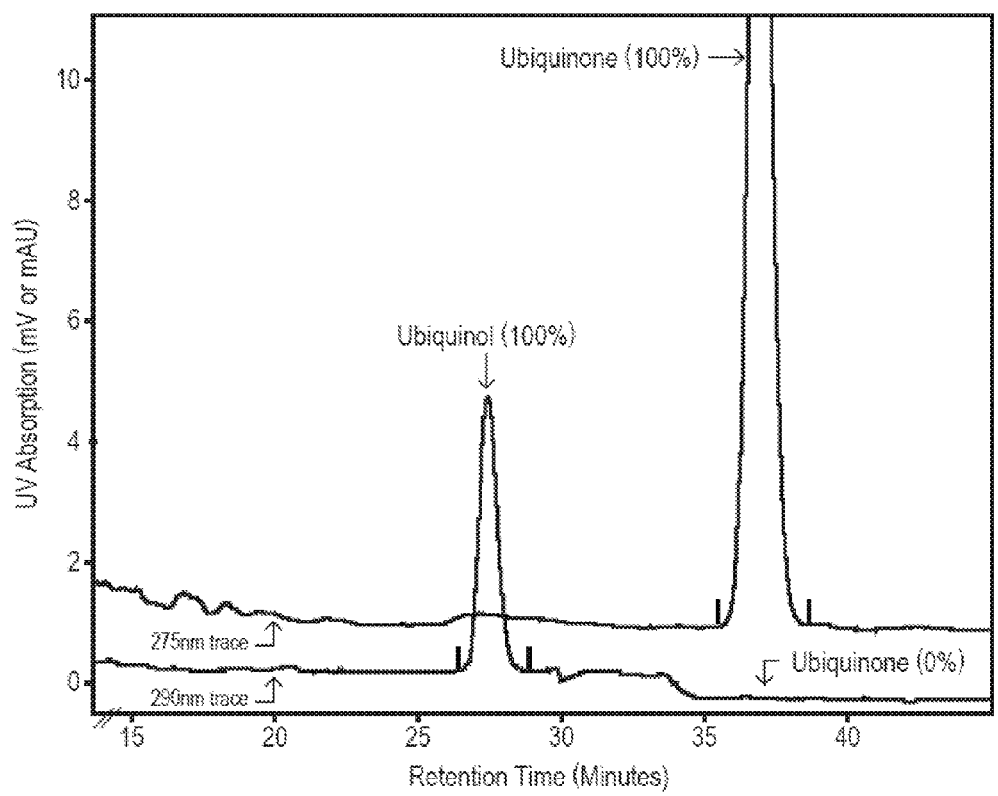
FIG. 3 illustrates HPLC analysis of a sample softgel containing 50 mg CoQ10 and 20 mg tocopherol. The analysis showed 100% ubiquinol and 0% ubiquinone when the UV was set at 290 nm (lower trace). The work-up sample was further deliberately oxidized, wherein all CoQ10 isomers converted to ubiquinone. HPLC analysis of this fully oxidized sample showed 100% ubiquinone when the UV was set at 275 nm (upper trace). This proves that vitamin E protects CoQ10 isomers from degradation and converts CoQ10 to the reduced ubiquinol.

All softgels with tocotrienols and/or tocopherols saw conversion of ubiquinone to ubiquinol and ubiquinol ranges from 24% to 86%. A typical chromatogram is seen in FIG. 2 and FIG. 3. This is unequivocal proof of the in situ conversion/reduction of the more stable oxidized state of CoQ10 (ubiquinone) to the less stable reduced state of CoQ10 (ubiquinol) by vitamin E molecules.

Example 2

Conditions were set as in Example 1. All encapsulated supplements with esterified vitamin E (e.g., alpha-tocopheryl acetate, alpha-tocopheryl succinate) saw zero conversion of ubiquinone to ubiquinol. Only vitamin E alcohols are effective.

Example 3

Figure 4:
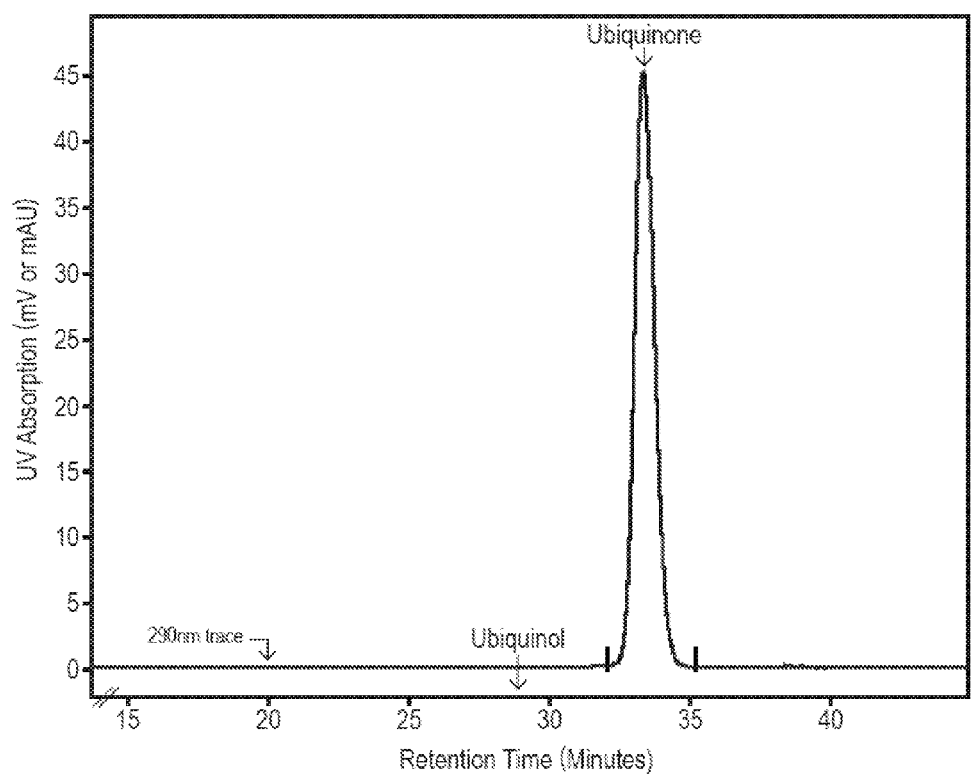
FIG. 4 illustrates HPLC analysis of a sample softgel containing 100 mg CoQ10 and 0 mg vitamin E. The analysis showed 0% ubiquinol and 100% ubiquinone when the UV was set at 290 nm, which is optimized for ubiquinol. Even so, no ubiquinol was detected, but only ubiquinone peaked. Further work-up procedure to oxidize the sample was not necessary. Therefore, without vitamin E (tocopherol or tocotrienol), CoQ10 ubiquinone did not convert to ubiquinol.

Conditions were set as in Example 1. Encapsulated supplements without tocopherol and/or tocotrienol saw zero conversion of ubiquinone to ubiquinol, as shown in FIG. 4. Furthermore, the amount of CoQ10 was diminished by 20% of the labeled value. Vitamin E protects from degradation of CoQ10, and without added vitamin E no ubiquinol was detected.

Example 4

Conditions were set as in Example 1. Encapsulated supplements with various sources of vitamin E were used to protect CoQ10, as shown in Table 2.

TABLE 2

| Encapsulated Supplements | Source Vitamin E Mixtures | CoQ10 Ratio (%) | |
|---|---|---|---|
| | | Ubiquinol | Ubiquinone |
| A | Annatto | 89 | 11 |
| B | Annatto + Palm + Soy | 74 | 26 |
| C | Palm + Soy | 24 | 76 |

Annatto contains the highest amount of tocotrienols, palm is intermediate, and soy contains the highest amount of tocopherols. Therefore, vitamin Es with a higher ratio of tocotrienol-to-tocopherol provides a higher ratio of ubiquinol-to-ubiquinone.

Example 5

CoQ10 is not very bioavailable and therefore many formulations are emulsified to enhance bioavailability with components such as beeswax, lecithin, and rice bran oil. Emulsification processes introduce significant undesirable oxidation. Encapsulated supplements of emulsified CoQ10 showed that all components were in the oxidized ubiquinone form. Applications of vitamin E will not only minimize the destruction of CoQ10 ubiquinone (Example 3), but also convert/reduce CoQ10 to the ubiquinol form.

A subject took 100 mg CoQ10 and 100 mg tocotrienol in a softgel formulation. Another subject took just 100 mg CoQ10. It is expected that when blood samples are compared between the subjects, the analysis shows that the subject taking the tocotrienol-CoQ10 combination have higher ubiquinone levels and a higher ubiquinol-to-ubiquinone ratio.

Example 6

100 mg CoQ10 (ubiquinone or ubiquinol), with and without tocotrienol, was placed in a beaker with acid (hydrochloric acid) (pH<2) for 30 minutes to simulate gastric conditions. In the presence of tocotrienol, the CoQ10 content (both ubiquinone or ubiquinol) was of higher content, thus ubiquinone resists acid-induced degradation.

Example 7

Various softgel formulations of CoQ10 ubiquinone (e.g., 10-180 mg/softgel) were made in combination with a) tocopherol, b) tocopherol-tocotrienol mixtures, and c) tocotrienol.

The analysis was done with numerous commercial samples of these two components in combination. For example, vitamin E formulations used tocotrienol alone (delta-tocotrienol and gamma-tocotrienol) commercially available tocotrienol (tocotrienol-tocopherol mixtures) and tocopherol alone (all variations). The CoQ10 formulations used ubiquinone (mainly) and ubiquinol (less frequently because it costs 4 times more than ubiquinone).

The softgel formulations were analyzed for CoQ10 subsequently. It was found that all vitamin E formulations converted/reduced ubiquinone to ubiquinol. The ubiquinol increases to about 50% (typically 25%-85%), and the amount of ubiquinol increases in relation to the amount tocotrienol.

Any source of tocopherol or tocotrienol can be used in preparing the formulations. Sources of tocopherol include soy, corn, cottonseed, and sunflower. Additionally several sources of tocopherol can be combined to obtain better combinations of isomers or a better commercial price. Sources of tocotrienol include rice, palm, and annatto. Once again, several sources of tocopherol can be combined to obtain better combinations of isomers or a better commercial price. Synthetic sources of tocotrienol (dl-tocotrienol) and tocopherol (dl-tocopherol) isomers can be used to prepare the formulations.

Vitamin E converts/reduces ubiquinone to ubiquinol in situ, that is, inside the softgels, prior to consumption/ingestion.

Example 8

Other known antioxidants can be used along with tocotrienols or in lieu of tocotrienol. Antioxidants, like epigallocatechin gallate (EGCG), resveratrol, and quercetin can be combined with CoQ10. This ensures that the antioxidants protect CoQ10 in situ and convert ubiquinone to ubiquinol.

Example 9

Tocotrienol and CoQ10 can be combined with omega-3 fatty acids (e.g., 100-1,500 mg/softgel). Sources of omega-3 fatty acids include, but are not limited to, marine, fish, krill, squid, seal, algal origins, and these omega-3 fatty acids may also be added to the combination.

Example 10

Tocotrienol and CoQ10 can be combined with lipids vitamins (A's, D's, E's, K's), isoprenoids, non-vitamins, antioxidants, and water-soluble vitamins (B's, C's).

Example 11

A softgel formulation of vitamin E (e.g., 50-300 mg/unit (softgel)) of tocopherol or tocotrienol) and vitamin A [retinol] (e.g., 500-5,000 IU/unit (softgel)) protects the retinol from oxidation to retinoic acid. When this formulation is consumed by a subject (mammal), the circulating vitamin E keeps vitamin A in its reduced state, as retinol.

REFERENCES

Lunetta, S. and M. Roman, Determination of coenzyme Q10 content in raw materials and dietary supplements by high-performance liquid chromatography-UV: collaborative study. J AOAC Int, 2008. 91(4): p. 702-8.

Kaplan, P., et al., Determination of coenzyme Q in human plasma. Physiol Res, 1996. 45(1): p. 39-45.

The invention claimed is:

1. A method of converting ubiquinone to ubiquinol; comprising the step of:
   mixing a tocopherol-free tocotrienol solution with a solution of ubiquinone, wherein the tocopherol-free tocotrienol is from a plant seed, wherein over 25% of the ubiquinone is converted to ubiquinol and wherein the weight to weight ratio of tocopherol-free tocotrienol to ubiquinone is less than 50%.

2. The method of claim 1, wherein over 50% of the ubiquinone is converted to ubiquinol.

3. The method of claim 2, wherein over 85% of the ubiquinone is converted to ubiquinol.

4. The method of claim 1, wherein the plant seed is annatto seed.

5. The method of claim 1, wherein the weight to weight ratio of tocopherol-free tocotrienol to ubiquinone is less than 36%.

6. The method of claim 5, wherein the weight to weight ratio of tocopherol-free tocotrienol to ubiquinone is less than 20%.

7. The method of claim 6, wherein the weight to weight ratio of tocopherol-free tocotrienol to ubiquinone is less than 6%.

* * * * *